United States Patent
Yoo et al.

(10) Patent No.: US 7,667,458 B2
(45) Date of Patent: Feb. 23, 2010

(54) PHANTOM FOR DIFFUSION TENSOR IMAGING

(75) Inventors: Done-Sik Yoo, Daejeon (KR);
 Yong-Min Chang, Daejeon (KR);
 Young-Jun Kim, Daejeon (KR);
 Seung-Hwan Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 12/096,355

(22) PCT Filed: Dec. 8, 2006

(86) PCT No.: PCT/KR2006/005307

§ 371 (c)(1),
(2), (4) Date: Jun. 5, 2008

(87) PCT Pub. No.: WO2007/066998

PCT Pub. Date: Jun. 14, 2007

(65) Prior Publication Data

US 2008/0284437 A1 Nov. 20, 2008

(30) Foreign Application Priority Data

Dec. 8, 2005 (KR) .................. 10-2005-0119525
Jun. 8, 2006 (KR) .................. 10-2006-0051459

(51) Int. Cl.
 *G01V 3/00* (2006.01)
(52) U.S. Cl. ........................ 324/308; 324/318
(58) Field of Classification Search ............ 324/308, 324/309, 318
See application file for complete search history.

(56) References Cited

U.S. PATENT DOCUMENTS

| | | | | |
|---|---|---|---|---|
| 5,312,755 | A * | 5/1994 | Madsen et al. | 436/8 |
| 6,318,146 | B1 * | 11/2001 | Madsen et al. | 73/1.86 |
| 6,409,515 | B1 | 6/2002 | Persohn et al. | |
| 6,493,574 | B1 | 12/2002 | Ehnholm et al. | |
| 6,720,766 | B2 * | 4/2004 | Parker et al. | 324/308 |
| 7,157,696 | B2 * | 1/2007 | White et al. | 250/252.1 |
| 2006/0195030 | A1 | 8/2006 | Ogrezeanu et al. | |
| 2008/0265882 | A1 * | 10/2008 | Wiggins | 324/308 |

FOREIGN PATENT DOCUMENTS

KR  1020040095467 A  11/2004

OTHER PUBLICATIONS

Korean Intellectual Property Office, International Search Report for International Application No., PCT/KR2006/005307, 3 pages. (Date completed: Mar. 19, 2007).

* cited by examiner

*Primary Examiner*—Louis M Arana

(57) ABSTRACT

A phantom for Diffusion Tensor Imaging (DTI) to measure the main physical quantities of diffusion tensors, such as diffusion anisotrophy, a diffusion principal axis and a route of the diffusion principal axis, and to evaluate the accuracy of DTI are provided. The phantom for diffusion tensor imaging includes: an outer container providing a space; materials for diffusion measurement located in the space of the outer container and formed of bunches of microtubes; and materials for fixing located in the space of the outer container to fix the materials for diffusion measurement to a specific location.

19 Claims, 3 Drawing Sheets

PHANTOM FOR DIFFUSION TENSOR IMAGING

CROSS REFERENCE TO RELATED APPLICATIONS

This application is a US National Stage of International Patent Application No. PCT/KR2006/005307, filed Dec. 8, 2006, which in turn claims the benefit of Korean Patent Application No. 10-2005-0119525, filed Dec. 8, 2005 and Korean Patent Application 10-2006-0051459, filed Jun. 8, 2006, the disclosures of all three applications are incorporated herein by reference.

TECHNICAL FIELD

The present invention relates to a phantom for Diffusion Tensor Imaging (DTI) to measure the main physical quantities of diffusion tensors, such as diffusion anisotropy, a diffusion principal axis and a route of the diffusion principal axis, and to evaluate the accuracy of DTI.

BACKGROUND ART

In general, when a brain disorder is suspected, Magnetic Resonance Imaging (MRI) is performed. Although MRI can provide anatomical images of the brain, it would not be easy to diagnose functional disorders due to neural injury. However, Diffusion Tensor Imaging (DTI) can capture functional images of the brain, and thus allows functional diagnosis.

Considering the principle that when an ink drop spreads in water, the ink diffuses in a circular shape according to the particle movement of the water, images of nerve cells of the brain are realized by measuring the diffusion direction and speed of water molecules. That is, if any part of the nerves of the brain is blocked or damaged, changes occur in the movement of water molecules in the neural tracks and thus neural damage in the brain can be detected. Therefore, unknown brain disorders can be diagnosed.

DTI is a new imaging method that closely examines the fine structure of biological tissue by anisotropy of diffusion, using the fact that the diffusion of water particles varies according to the structure of biological tissue. An advantage of DTI is showed in the diagnosis of diseases that are not found out by general medical imaging, such as disorder in the fine structure of brain white matter. Therefore, DTI is very important for neuroscience and also clinical study.

In particular, DTI is very useful in the diagnosis of degenerative brain diseases such as dementia, which are not visible to current imaging technologies. Currently, computerized localizing of normal tissue and damaged tissue has been progressed in developed countries for quantification of DTI.

DISCLOSURE OF INVENTION

Technical Problem

Development of a standard phantom is necessary to find out the accuracy of DTI images. A quantity of diffusion tensor in the structure of the brain's white matter varies according to age group and also varies between normal people and patients and ethnic group. Therefore, development of a DTI standard phantom is urgently required to determine whether DTI detects the diffusion tensor accurately.

SUMMARY OF THE INVENTION

Technical Solution

The present invention provides a phantom for Diffusion Tensor Imaging (DTI) to measure the main physical quantities of diffusion tensors, such as diffusion anisotropy, a diffusion principal axis and a route of the diffusion principal axis, and to evaluate the accuracy of DTI.

According to an aspect of the present invention, there is provided a phantom for diffusion tensor imaging, including: an outer container providing a space; materials for diffusion measurement located in the space of the outer container and formed of bunches of microtubes; and materials for fixing located in the space of the outer container to fix the materials for diffusion measurement to a specific location.

The outer container may be formed of acrylic resin.

The acrylic resin may be selected from the group consisting of polymethylacrylate, polymethylmethacrylate, and copolymer of methylacrylate and methylmethacrylate.

The microtubes may have a diameter of 10 um or less.

The materials for diffusion measurement may be natural fibrous materials including bunches of microtubes.

The materials for diffusion measurement may be non-metallic tubes having a diameter of 1 cm or less, wherein micro beads, which expand by moisture absorption, are charged in the materials for diffusion measurement.

The materials for diffusion measurement may be a spiral shape located in the center of the outer container and linear shapes located at the edges of the outer container.

The materials for fixing may be liquefied by warming and solidified by cooling.

The materials for fixing may be one of liquefied acrylic resin and paraffin.

According to another aspect of the present invention, there is provided a phantom for diffusion tensor imaging comprising: a first diffusion tensor measuring unit; and a second diffusion tensor measuring unit, wherein the first diffusion tensor measuring unit comprises a first outer container, first materials for diffusion measurement located inside the outer container and formed of bunches of first microtubes, and first materials for fixing located inside the first outer container to fix the first materials for diffusion measurement to a specific location, wherein the second diffusion tensor measuring unit includes a second outer container, second materials for diffusion measurement located inside the outer container and formed of bunches of second microtubes, and second materials for fixing located inside the second outer container to fix the second materials for diffusion measurement to a specific location, wherein the first diffusion tensor measuring unit is laminated onto the second diffusion tensor measuring unit, and wherein the first microtubes and the second microtubes have different diameters.

The outer container may be formed of acrylic resin.

The acrylic resin may be selected from the group consisting of polymethylacrylate, polymethylacrylate, and copolymer of methylacrylate and methylmethacrylate.

The microtubes may have a diameter of 10 um or less.

The materials for diffusion measurement may be natural fibrous materials including bunches of microtubes.

The materials for diffusion measurement may be non-metallic tubes having a diameter of 1 cm or less, wherein micro beads, which expand by moisture absorption, are charged in the materials for diffusion measurement.

The materials for diffusion measurement may be a spiral shape located in the center of the outer container and linear shapes located at the edges of the outer container.

The materials for fixing may be liquefied by warming and solidified by cooling.

The materials for fixing are one of liquefied acrylic resin and paraffin.

ADVANTAGEOUS EFFECTS

As described above, the phantom for diffusion tensor imaging according to an embodiment of the present invention can measure the main physical quantities of diffusion tensors, such as diffusion anisotropy, a diffusion principal axis and a route of the diffusion principal axis, and evaluate the accuracy of DT. Therefore, the phantom for diffusion tensor imaging of the present invention can be used to maintain the high quality of the imaging method.

DESCRIPTION OF DRAWINGS

The above and other features and advantages of the present invention will become more apparent by describing in detail exemplary embodiments thereof with reference to the attached drawings in which.

BEST MODE

Detailed Description of the Invention

The present invention will now be described more fully with reference to the accompanying drawings, in which exemplary embodiments of the invention are shown.

Figure 1:
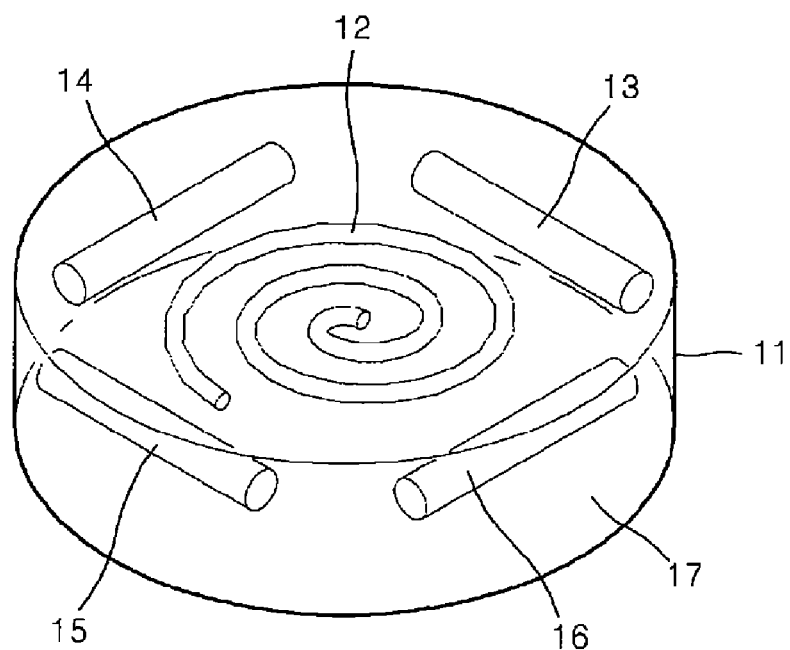
FIG. 1 is a perspective view of a phantom for diffusion tensor imaging according to an embodiment of the present invention.
Figure 2:
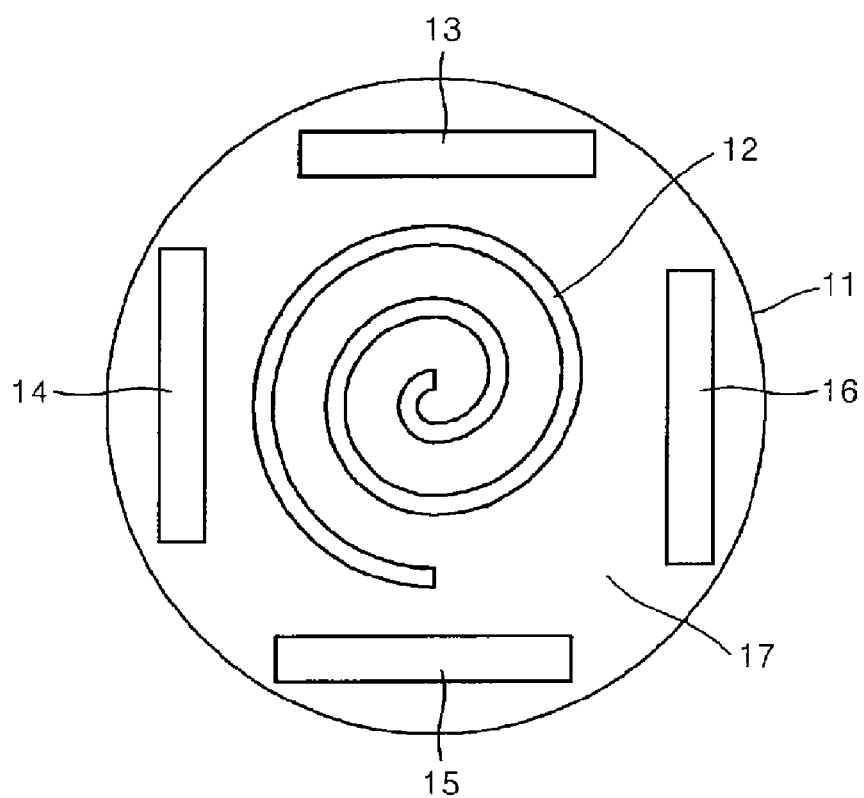
FIG. 2 is a cross sectional view of the upper part of the phantom for diffusion tensor imaging of FIG. 1.

FIG. 1 is a perspective view of a phantom for diffusion tensor imaging according to an embodiment of the present invention, and FIG. 2 is a cross sectional view of the upper part of the phantom for diffusion tensor imaging of FIG. 1.

Referring to FIGS. 1 and 2, a phantom for diffusion tensor imaging is formed of an outer container 11, materials for diffusion measurement 12 through 16, and materials for fixing 17.

The outer container 11 includes materials for diffusion measurement 12 through 16 and materials for fixing 17.

The outer container 11 may be formed of acrylic resin or non-metallic materials which are not breakable by external shock and are not sensitive to temperature changes.

The acrylic resin may be selected from the group consisting of polymethylacrylate, polymethylmethacrylate, and copolymer of methylacrylate and methylenethacrylate.

The materials for diffusion measurement 12 through 16 are located inside the outer container 11 and are formed of bunches of microtubes, which have a diameter of 10 um or less.

The materials for diffusion measurement 12 through 16 may be natural fibrous materials including bunches of microtubes. For example, the natural fibrous materials including bunches of microtubes may be stems of various plants such as leaves of vegetables or a bamboo stem.

In addition, the materials for diffusion measurement 12 through 16 may be muscle tissue of animals. However, the natural fibrous materials and the muscle tissue of animals are perishable, and thus are used for one-time use, instead of long-term use.

Moreover, the materials for diffusion measurement 12 through 16 may be non-metallic tubes having a diameter of 1 cm or less, wherein micro beads, which expand by moisture absorption, are charged in the materials for diffusion measurement. Dried micro beads are charged to the non-metallic tubes, and then distilled water is added to hydrate the micro beads, thereby manufacturing tubes having micro beads.

The materials for diffusion measurement 12 through 16 may be a spiral shape 12 located in the center of the outer container 11 and linear shapes 13, 14, 15, and 16 located at the edges of the outer container 11. This arrangement has the advantages of accurately measuring anisotropy of the diffusion tensor and providing directional information of the principal axis of the diffusion tensor. In addition, both rectangular and elliptical shapes are possible.

The materials for fixing 17 are located in the outer container 11, and fix the materials for diffusion measurement 12 through 16 to a specific location. The materials for fixing 17 can occupy the space in the outer container 11 which is not occupied by the materials for diffusion measurement 12 through 16.

In order to easily manufacture the phantom for diffusion tensor imaging according to an embodiment of the present invention, the materials for fixing 17 may be liquefied by warming and solidified by cooling. For example, the materials for fixing 17 may be liquefied acrylic resin or paraffin.

An operating process of the phantom for diffusion tensor imaging according to an embodiment of the present invention will now be described.

First, the phantom for diffusion tensor imaging is installed in a coil for brain installed in an MRI magnet bore, and then the coil is moved to the right center of the magnet to obtain a localization image. Next, an anatomical T2 image is obtained using the localization image before a diffusion weighted image is obtained using a DTI pulse sequence in a spin-echo EPI series. Then, a diffusion tensor image is created through post image processing the obtained diffusion tensor image, based on a mathematical model.

Figure 3:
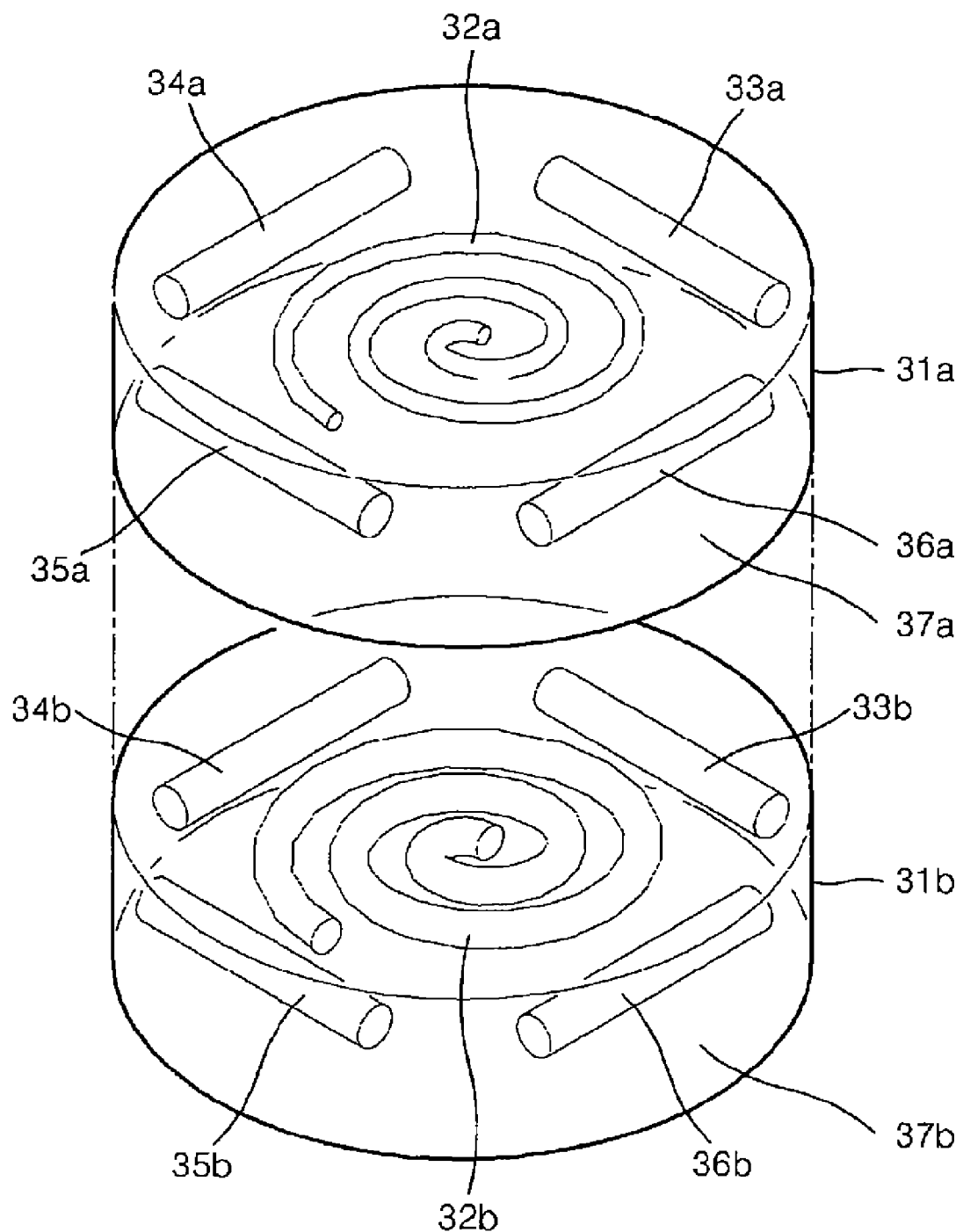
FIG. 3 is a perspective view of a phantom for diffusion tensor imaging according to another embodiment of the present invention.
Figure 4:
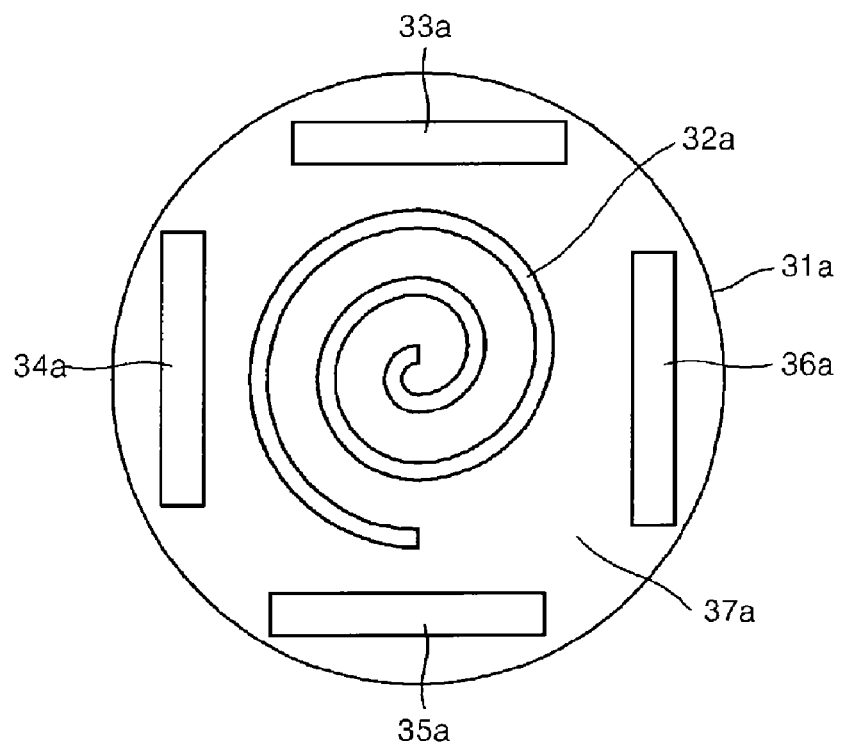
FIG. 4 is a cross sectional view of the upper part of the phantom for diffusion tensor imaging of FIG. 3.

FIG. 3 is a perspective view of a phantom for diffusion tensor imaging according to another embodiment of the present invention. FIG. 4 is a cross sectional view of the upper part of the phantom for diffusion tensor imaging of FIG. 3, and FIG. 5 is a cross sectional view of the lower part of the phantom for diffusion tensor imaging of FIG. 3.

Figure 5:
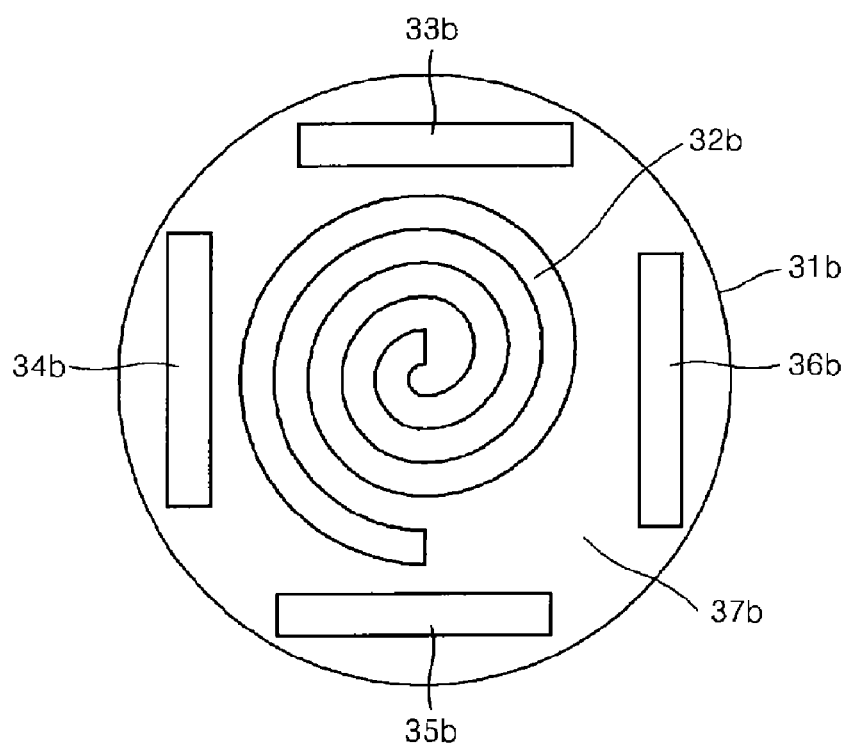
FIG. 5 is a cross sectional view of the lower part of the phantom for diffusion tensor imaging of FIG. 3.

The phantom for diffusion tensor imaging of FIGS. 3 through 5 is a laminated form of the two phantoms for diffusion tensor imaging illustrated in FIGS. 1 and 2.

Referring to FIGS. 3 through 5, the phantom for diffusion tensor imaging includes a first diffusion tensor measuring unit and a second diffusion tensor measuring unit, wherein the first diffusion tensor measuring unit includes a first outer container 31A, first materials for diffusion measurement 32A through 36A located inside the outer container 31A and formed of bunches of first microtubes, and first materials for fixing 37A located inside the first outer container 31A to fix the first materials for diffusion measurement 32A through 36A to a specific location, and wherein the second diffusion tensor measuring unit includes a second outer container 31B, second materials for diffusion measurement 32B through 36B located inside the outer container 31B and formed of bunches of second microtubes, and second materials for fixing 37B located inside the second outer container 31B to fix the second materials for diffusion measurement 32B through 36B to a specific location. The first diffusion tensor measuring unit is laminated onto the second diffusion tensor measuring unit.

Referring to FIGS. 4 and 5, the first microtubes and the second microtubes have different diameters. In addition, the arrangement of the first materials for diffusion measurement 32A through 36A and the second materials for diffusion measurement 32B through 36B may be same or different.

As illustrated in FIGS. 3 and 5, when the two phantoms for diffusion tensor imaging are laminated, the arrangement of materials for diffusion measurement differs, and/or the diameters of microtubes differ, the direction of the diffusion tensor and the minimum resolution of the DTI are improved.

While the present invention has been particularly shown and described with reference to exemplary embodiments thereof, it will be understood by those of ordinary skill in the art that various changes in form and detail may be made therein without departing from the spirit and scope of the present invention as defined by the following claims.

The invention claimed is:

1. A phantom for diffusion tensor imaging, comprising:
 a plurality of diffusion measurement components provided within a predefined space, each diffusion measurement component having microtubes; and
 solidified material provided within the space and configured to securely position the diffusion measurement components at designated locations within the space,
 wherein the diffusion measurement components and the solidified material substantially define the space.

2. The phantom for diffusion tensor imaging of claim 1, wherein the solidified material is formed of acrylic resin that has been solidified, and
 wherein the phantom for diffusion tensor imaging further comprising:
 a container defining a space wherein the diffusion measurement components and the solidified material are provided.

3. The phantom for diffusion tensor imaging of claim 2, wherein the acrylic resin is selected from the group consisting of polymethylacrylate, polymethylmethacrylate, and copolymer of methylacrylate and methylmethacrylate,
 wherein the solidified material and the diffusion measurement components substantially fill the space defined by the container.

4. The phantom for diffusion tensor imaging of claim 1, wherein the microtubes have a diameter of 10 um or less.

5. The phantom for diffusion tensor imaging of claim 1, wherein the diffusion measurement components include natural fibrous materials.

6. The phantom for diffusion tensor imaging of claim 5, wherein the container and the solidified material are made substantially the same material, and
 wherein the solidified material defines the container.

7. The phantom for diffusion tensor imaging of claim 1, wherein the diffusion measurement components are non-metallic tubes having a diameter of 1 cm or less, the diffusion measurement components having micro beads that expand by moisture absorption.

8. The phantom for diffusion tensor imaging of claim 1, wherein the diffusion measurement components includes a spiral shaped component located at a midsection of the phantom for diffusion tensor imaging and a plurality of linear shaped components located proximate edges of the phantom for diffusion tensor imaging.

9. The phantom for diffusion tensor imaging of claim 1, wherein the material has been solidified to securely position the diffusion measurement components at the designated locations within the space.

10. The phantom for diffusion tensor imaging of claim 1, wherein the phantom for diffusion tensor imaging further comprising a container wherein the diffusion measurement components and the solidified material are provided,
 wherein the solidified material has been solidified to securely position the diffusion measurement components at the designated locations within the space, and
 wherein the phantom for diffusion tensor imaging consists essentially of the container, the diffusion measurement components, and the solidified material.

11. A phantom for diffusion tensor imaging comprising:
 a first diffusion tensor measuring unit, the first diffusion tensor measuring unit comprising:
 a first container defining a first space therein,
 first diffusion measurement components provided within the first space of the container and having a plurality of first microtubes, and
 first solid material to securely place the first diffusion measurement components to designated locations within the first space of the first container, the first solid material filling the first space of the first container and having outer dimensions corresponding to the first space of the first container; and
 a second diffusion tensor measuring unit, the second diffusion tensor measuring unit comprising:
 a second container defining a second space therein,
 second diffusion measurement components provided within the second space of the container and having a plurality of second microtubes, and
 second solid material to securely place the second diffusion measurement components to designated locations within the second space of the second container, the second solid material filling the second space of the second container and having outer dimensions corresponding to the second space of the second container,
 wherein the first diffusion tensor measuring unit is laminated onto the second diffusion tensor measuring unit, and
 wherein the first microtubes and the second microtubes have different diameters.

12. The phantom for diffusion tensor imaging of claim 11, wherein the first container is formed of acrylic resin.

13. The phantom for diffusion tensor imaging of claim 12, wherein the acrylic resin is selected from the group consisting of polymethylacrylate, polymethylmethacrylate, and copolymer of methylacrylate and methylmethacrylate.

14. The phantom for diffusion tensor imaging of claim 11, wherein the first microtubes have a diameter of 10 um or less.

15. The phantom for diffusion tensor imaging of claim 11, wherein the first diffusion measurement components include natural fibrous materials having first microtubes.

16. The phantom for diffusion tensor imaging of claim 11, wherein the first diffusion measurement components are non-metallic tubes having a diameter of 1 cm or less and including micro beads that expand by moisture absorption.

17. The phantom for diffusion tensor imaging of claim 11, wherein the first diffusion measurement components include a spiral shaped component located proximate a midsection of the first container and a plurality of linear shaped components located proximate edges of the first container.

18. The phantom for diffusion tensor imaging of claim 11, wherein the first solid material has a characteristic of being liquefied when heated and solidified when cooled.

19. The phantom for diffusion tensor imaging of claim 11, wherein the first solid material includes acrylic resin or paraffin.

* * * * *